United States Patent [19]

McCarthy et al.

[11] Patent Number: 5,116,368
[45] Date of Patent: May 26, 1992

[54] POLYPEPTIDES WITH FIBRONECTIN ACTIVITY

[75] Inventors: James B. McCarthy; Leo T. Furcht, both of Minneapolis, Minn.

[73] Assignee: Regents of the University of Minnesota, Minneapolis, Minn.

[21] Appl. No.: 326,279

[22] Filed: Mar. 21, 1989

Related U.S. Application Data

[62] Division of Ser. No. 89,073, Aug. 25, 1987, Pat. No. 4,839,464.

[51] Int. Cl.$^5$ .......................... C07K 7/08; A61F 2/16; A61F 2/02
[52] U.S. Cl. ............................. 623/2; 623/3; 623/4; 623/6; 623/22; 623/1; 530/326; 514/13
[58] Field of Search .................... D24/33; 623/2, 3, 4, 623/6, 22

[56] References Cited

U.S. PATENT DOCUMENTS

| | | | |
|---|---|---|---|
| 3,966,902 | 6/1976 | Chromecek | 424/59 |
| 4,517,686 | 5/1985 | Ruoslahti et al. | 3/1 |
| 4,578,079 | 3/1986 | Ruoslahti et al. | 623/11 |

OTHER PUBLICATIONS

M. D. Pierschbacher et al., *PNAS USA*, 81, 5985–5988 (1984).
J. B. McCarthy et al., *J. Cell Biol.*, 102, 179–188 (1986).
A. R. Kornblihtt et al., *EMBO J.*, 4, 1755–1759 (1985).
T. E. Petersen et al., *PNAS USA*, 80, 137–141 (1983).
J. E. Schwarzbauer et al., *Cell*, 35, 421–431 (1983).
D. E. Smith and L. T. Furcht, *J. Biol. Chem.*, 257, 6518–6523 (1982).
S. L. Rogers et al., *Devel. Biol.*, 98, 212–220 (1983).
H. K. Kambic et al., *Chem. and Eng. News*, 30–48 (Apr. 14, 1986).
L. T. Furcht, *Modern Cell Biology*, vol. 1, B. Satir, ed., Alan R. Liss, Inc., New York (1983) at 53–117.
L. Furcht et al., *Biochem. and Molec. Genetics of Cancer Metastasis*, K. Lapis et al., eds., (1985) at pp. 43–53.
A. Garcia-Pardo et al., *Biochem. J.*, 241, 923–928 (1987).
R. M. Hewick et al., *J. Biol. Chem.*, 256, 7990–7997 (1981).
M. J. Humphries et al., *J. Biol. Chem.*, 262, 6886–6892 (1987).
J. Kyte et al., *J. Mol. Biol.*, 157, 105–132 (1982).
H. Pande et al., *Eur. J. Biochem.*, 162, 403–411 (1987).
S. M. Schwartz, *In Vitro*, 14, 966–980 (1978).

*Primary Examiner*—Johann Richter
*Attorney, Agent, or Firm*—Merchant, Gould, Smith, Edell, Welter & Schmidt

[57] ABSTRACT

A composition which can bind heparin and promote cellular adhesion and neurite outgrowth is provided which consists essentially of a polypeptide of the formula:

tyr—glu—lys—pro—gly—ser—pro—pro—arg—glu—val—val—pro—arg—pro—arg—pro—gly—val, lys—asn—asn—gln—lys—ser—glu—pro—leu—ileu—gly—arg—lys—lys—thr—asp—glu—leu, or mixtures thereof.

Medical devices such as prosthetic implants, percutaneous devices and cell culture substrates coated with the polypeptide composition are also provided.

9 Claims, 3 Drawing Sheets

FIG. 4

1) ----------TAGPDQTEMTIEGLQPTVEYVVSVYAQNPSGESQPLVQTAVT/
                               1583↑

2) AIPAPTDLKFTQVTPTSLSAQWTPPNVQLTGYRVRVTPREKTGPMKEINLAPDSSSVVVSGLMVATKYEVSVYALKDTLTSRPAQGVVTTLE

3) NVSPPRRARVTDATETTITISWRTKTETITGFQVDAVPANGQTPIQRTIKPDVRSYTITGLQPGTDYKIYLYTLNDNARSSPVVIDAST

4) AIDAPSNLRFLATTPNSLLVSWQPPRARITGYIIKYEKPGSPPREVVPRPGVTEATITGLEPGTEYTIYVIALKNNQKSEPLIGRKKT

5) DELPQLVTLPHPNLHGPEILDVPSTVQKTPFVTHPGYDTGNGIQLPGTSGQQPSVGQQMIFEEHGFRRTTPPTTATPIRHRPRPYPPNV(GEEIQIGHIPREDVDYHLYPHGPGLNPNAST)
                                                                                                          2040↑

6) GQEALSQTTISWTPF----------

POLYPEPTIDES WITH FIBRONECTIN ACTIVITY

BACKGROUND OF THE INVENTION

The present invention was made with the support of Grant No. CA21463 from the National Institutes of Health. The Government has certain rights in the invention.

This is a division, of application Ser. No. 89,073, filed Aug. 25, 1987, now U.S. Pat. No. 4,839,464.

The adhesion of mammalian cells to the extracellular matrix is of fundamental importance in regulating growth, adhesion, motility and the development of proper cellular phenotype. This has implications for normal development, wound healing, chronic inflammatory diseases, and tumor metastasis. Evidence accumulated over the last several years suggests that the molecular basis for the adhesion of both normal and transformed cells is complex and probably involves several distinct cell surface molecules. Extracellular matrices consist of three types of macromolecules: collagens, proteoglycans and noncollagenous glycoproteins. The extracellular matrix molecule which has been most intensively studied with regard to cell adhesion is the noncollagenous cell adhesion glycoprotein, fibronectin, which is present in plasma, cell matrices, basal lamina and on cell surfaces. The plasma form of fibronectin consists of a disulfide-bonded dimer having a molecular weight of 450,000 daltons. The two subunit chains ("A" and "B"), each of about 220,000 daltons, are observed under reducing conditions. This form of fibronectin will be referred to as "fibronectin" hereinafter.

Fibronectin, as with other components of the extracellular matrix, has the ability to bind to itself, to other matrix constituents, and to the surface of cells, via discrete domains on the molecule. For example, fibronectin promotes the attachment of suspended cells to collagen. (See L. T. Furcht, *Modern Cell Biology*, B. Satir, ed., Alan R. Liss, Inc., N.Y., Vol. I (1983) at pages 53-117). The primary structure of one adhesion sequence within fibronectin was originally deduced by M. D. Pierschbacher et al. using monoclonal antibody data and direct sequence analysis. This sequence was found to be a tetrapeptide consisting of arginyl-glycyl-aspartyl-serine (RGDS) (M. D. Pierschbacher and E. Ruoslahti, *PNAS USA*, 81, 5985 (1984)). Peptides containing the RGDS sequence are capable of directly promoting the adhesion of certain cell types, and high levels of soluble RGDS will partially disrupt cell adhesion to intact fibronectin. Cell adhesion to the RGDS sequence in fibronectin is believed to occur by the interaction of this sequence with a cell surface glycoprotein complex termed "integrin".

Despite the importance of the RGDS/integrin complex in fibronectin mediated cell adhesion, several lines of evidence point to the involvement of additional cellular receptors and different fibronectin determinants in this process. Many cell types form focal adhesions on intact fibronectin. These structures represent regions of close apposition between the plasma membrane and the substratum. These sites also represent insertion points for actin-rich stress fibers, and have been shown to contain several actin-associated cytoskeletal proteins. Focal adhesion sites also contain several classes of cell surface molecules implicated in cell adhesion, including integrin, heparan sulfate, chondroitin sulfate, or other proteoglycans and gangliosides.

The action of multiple receptors for fibronectin has been implicated in adhesion plaque formation. Cells adherent to either RGDS-containing fragments or heparin-binding, adhesion promoting ligands (e.g., platelet factor 4 or heparin binding fragments of fibronectin) form only close contacts. In contrast, cells adherent on both RGDS-containing fragments and heparin binding ligands display fully developed focal adhesions. Additionally, antibodies against heparin binding fragments of fibronectin inhibit focal adhesion formation, without drastically inhibiting the level of cell adhesion on intact fibronectin. Collectively, these results support a role of heparin binding domain(s) of fibronectin in promoting normal and malignant cell adhesion, and in regulating phenotypic expression of cells.

J. B. McCarthy et al., in *J. Cell Biol.*, 102, 179 (1986) recently published results identifying a 33 kD carboxyl terminal heparin binding fragment of fibronectin which promotes the adhesion and spreading of metastatic melanoma cells by an RGDS independent mechanism. This fragment originates from the A chain of the fibronectin molecule. It binds heparan sulfate proteoglycan and also promotes the adhesion of neurons and the extension of neurites by these cells.

Therefore, a need exists to isolate and characterize the subset of peptides within this fragment which are responsible for its wide range of biological activities. Such lower molecular weight oligopeptides would be expected to be more readily obtainable and to exhibit a narrower profile of biological activity than the 33 kD fragment, thus increasing their potential usefulness as therapeutic or diagnostic agents.

BRIEF DESCRIPTION OF THE INVENTION

The present invention provides two polypeptides which represent fragments of the 33 kD carboxyl terminal, heparin-binding region located on the A chain of fibronectin. The polypeptides, which can be prepared by conventional solid phase peptide synthesis, have the formulas:

(I)
tyr—glu—lys—pro—gly—ser—pro—pro—arg—glu—val—val—pro—arg—pro—arg—pro—gly—val and (II)
lys—asn—asn—gln—lys—ser—glu—pro—leu—ileu—gly—arg—lys—lys—thr—asp—glu—leu Polypeptide I formally represents isolated fibronectin residues 1906-1924, while polypeptide II formally represents isolated fibronectin residues 1946-1963. The single letter amino acid codes for these polypeptides are YEKPGSPPREVVPRPRPGV and KNNQKSEPLIGRKKTDEL.

These synthetic polypeptides were assayed for bioactivity and found to (a) promote neurite extension, and to promote the adhesion and spreading of (b) endothelial cells, (c) melanoma cells and (d) heparin binding to a synthetic substrate (II only). Therefore, it is believed that these polypeptides may be useful to (a) assist in nerve regeneration, (b) promote wound healing and implant acceptance, (c) promote cellular attachment to culture substrata and (d) inhibit the metastasis of malignant cells. Due to the difference in the spectra of biological activities exhibited by polypeptides I and II, mixtures of I and II are also within the scope of the invention.

Furthermore, since it is expected that further digestion/hydrolysis of polypeptides I and II in vitro or in vivo will yield fragments of substantially equivalent bioactivity, such lower molecular weight polypeptides are considered to be within the scope of the present invention.

BRIEF DESCRIPTION OF THE DRAWINGS

FIG. 4 is a schematic representation of the amino acid sequence of a portion of the plasma fibronectin molecule.

DETAILED DESCRIPTION OF THE INVENTION

Structure of Fibronectin

Figure 1:
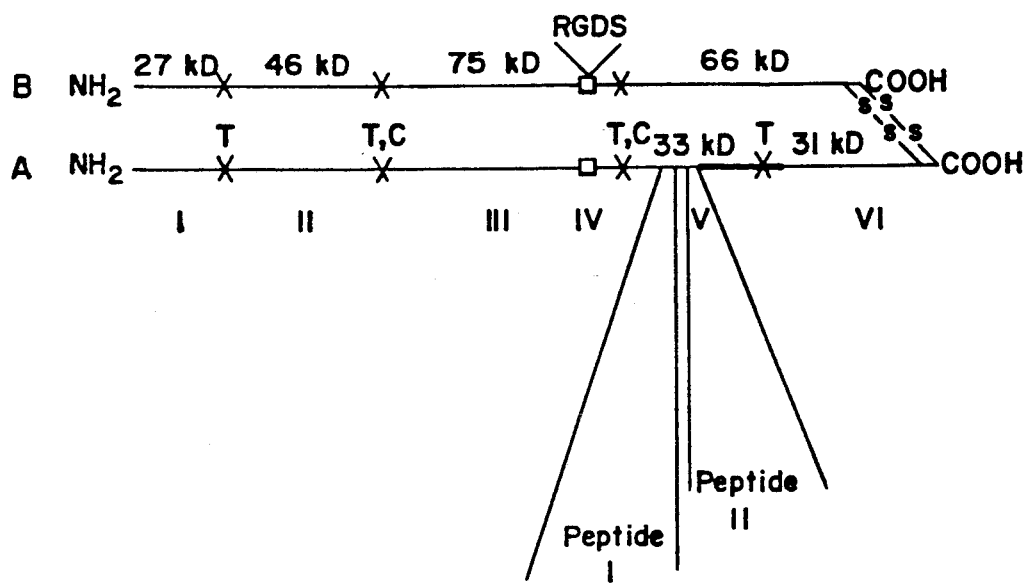
FIG. 1 is a schematic depiction of plasma fibronectin, indicating the relative location of RGDS on the B chain with respect to peptides I and II of the present invention, which are located on the 33 kD carboxyl terminal heparin binding fragment of the A chain.

Referring to FIG. 1, the two types of chains (A and B) of plasma fibronectin are shown as a disulfide (-S-S-) bonded heterodimer. The six domains (I–VI) of fibronectin are labeled according to previous nomenclature (L. T. Furcht in *Modern Cell Biology*, B. Satir, ed., Alan R. Liss, Inc., NY (1983) at pages 53–117.) Biological activities within each domain include: (I) weak heparin binding, (II) noncovalent collagen binding, (III) DNA binding, (IV) RGDS-mediated cell adhesion, shown as box (O), (V) heparin binding, RGDS independent cell adhesion, and (VI) free sulfhydryl. The molecular weight estimates of proteolytic fragments containing each domain are based on a previously described digestion and purification scheme. (J. B. McCarthy, *J. Cell Biol.*, 102, 179 (1986)). Proteolytic cleavage sites (X) are shown for trypsin (T) and Cathepsin D (C). By these schemes, domains V and VI isolated from digests of the B chain are located on a 66 kD fragment. In contrast, the A chain digests contain a 33 kD fragment (domain V) and a 31 kD fragment (domain VI). The difference is a result of a trypsin sensitive site in the A-chain specific type IIIcs insert, shown as a bold line.

Amino Terminal Sequence of the Tryptic/Catheptic 66K and 33K Heparin Binding Fragments and Carboxyl Terminal Tryptic 31K Free-Sulfhydryl Containing Fragment.

The entire primary structure of fibronectin has either been determined directly (T. E. Peterson et al., *PNAS USA*, 80, 137 (1983)) or has been predicted from recombinant DNA technology. (J. E. Schwarzbauer et al., *Cell*, 135, 421 (1983)). The amino terminal sequences of tryptic/catheptic (t/c) 33 kD, t/c66 kD, and tryptic (t) 31 kD fragments were established by direct amino acid sequencing on an Applied Biosystems gas phase sequenator (Model 470A), in order to determine the exact location of these fragments with respect to the known human sequence.

The first 21 amino acids which were determined for the t/c66 heparin binding fragment (FIG. 4, underlined residues which begin in line 1 and continue in line 2). This fragment starts with the amino acid alanine which corresponds to residue 1583 on intact plasma fibronectin (A. R. Kornblihtt et al., *EMBO J.*, 4, 1755 (1985)). The presence of tyrosine to the amino terminal side of this alanine in intact fibronectin is consistent with a preference of Cathepsin D for peptide bonds involving aromatic residues. The sequence of the t/c66 fragment does not contain the EDIII insert, since the sequence proceeds from a threonine at residue number 1599 (double asterisks followed by a slash at the end of line 1) to an alanine at residue 1690 (first residue, line 2). This lack of the EDIII region is a characteristic feature which distinguishes plasma- or liver-derived fibronectin from cellular, or fibroblast derived fibronectin.

The t/c33 fragment also shares a common amino terminal sequence with the t/c66 fragment (FIG. 4, line 1), beginning with alanine at position 1583 and it also lacks the EDIII domain. These results illustrate that the amino terminal sequences of these fragments are identical, and support the contention that the size heterogeneity of the t/c33 and t/c66 heparin binding fragments results from the action of trypsin within the type IIIcs insert of the A chains of plasma fibronectin.

Localization of the 33 kD heparin binding fragment within the A chain of plasma fibronectin was established by determining the amino terminal sequence of the first 21 amino acids of a tryptic 31 kD fragment. This fragment, which is produced during the purification of 33 and 66 kD heparin binding fragments, contains a free sulfhydryl and orginates from the carboxyl terminal end of the A chain of plasma fibronectin. See D. E. Smith and L. T. Furcht, *J. Biol. Chem.*, 257, 6518 (1982). Furthermore, the 31 kD fragment also originates from a subset of fibronectin molecules which give rise to the 33 kD heparin binding fragment of fibronectin.

The amino terminal end of the t31 fragment begins at histidine residue 2040, underlined, line 5 of FIG. 4. This is consistent with the known specificities of trypsin, since the residue to the amino terminal side of this histidine is an arginine. This sequence is present in the type IIIcs insert which occurs in a subset of fibronectin molecules. This fragment contains 9 additional amino acids from the type IIIcs insert, skips the last 31 amino acids of this insert (FIG. 4, line 5, parentheses), then continues as a type III homology (FIG. 4, line 6, underlined) until the tyrosine at residue 2062 where the current sequence information ends. These results demonstrate that the t31 fragment contains a portion (the first 89 amino acids) of the maximum possible 120 residue type IIIcs inserted sequence, in agreement with previously established sequence data for this region of plasma fibronectin. The sequence information indicates the maximum possible carboxyl terminal limit of the t/c33 heparin binding fragment at arginine residue 2039, within the type IIIcs insert (FIG. 4, line 5).

Two polypeptides, which represent sequences present within this region, were synthesized as described hereinbelow.

Synthesis of Polypeptides

The polypeptides of the invention were synthesized using the Merrifield solid phase method. This is the method most commonly used for peptide synthesis, and it is extensively described by J. M. Stewart and J. D. Young in *Solid Phase Peptide Synthesis*, Pierce Chemical Company, pub., Rockford, Il (2d ed., 1984), the disclosure of which is incorporated by reference herein.

The Merrifield system of peptide synthesis uses a 1% crosslinked polystyrene resin functionalized with benzyl chloride groups. The halogens, when reacted with the salt of a protected amino acid will form an ester, linking it covalently to the resin. The benzyloxy-carbonyl (BOC) group is used to protect the free amino group of the amino acid. This protecting group is removed with 25% trifluoroacetic acid (TCA) in dichloromethane (DCM). The newly exposed amino group is converted to the free base by 10% triethylamine (TEA) in DCM. The next BOC-protected amino acid is then coupled to the free amine of the previous amino acid by the use of dicyclohexylcarbodiimide (DCC). Side chain functional groups of the amino acids are protected during synthesis by TFA stable benzyl derivatives. All of these repetitive reactions can be automated, and the peptides of the present invention were synthesized at the University of Minnesota Microchemical facility by the use of a Beckman System 990 Peptide synthesizer.

Following synthesis of a blocked polypeptide on the resin, the polypeptide resin is treated with anhydrous hydrofluoric acid (HF) to cleave the benzyl ester linkage to the resin and thus to release the free polypeptide. The benzyl-derived side chain protecting groups are also removed by the HF treatment. The polypeptide is then extracted from the resin, using 1.0M acetic acid, followed by lyophilization of the extract.

Lyophilized crude polypeptides are purified by preparative high performance liquid chromatography (HPLC) by reverse phase technique on a C-18 column. A typical elution gradient is 0% to 60% acetonitrile with 0.1% TFA in $H_2O$. Absorbance of the eluant is monitored at 220 nm, and fractions are collected and lyophilized.

Characterization of the purified polypeptide is by amino acid analysis. The polypeptides are first hydrolyzed anaerobically for 24 hours at 110° C. in 6M HCl (constant boiling) or in 4N methanesulfonic acid, when cysteine or tryptophane are present. The hydrolyzed amino acids are separated by ion exchange chromatography using a Beckman System 6300 amino acid analyzer, using citrate buffers supplied by Beckman. Quantitation is by absorbance at 440 and 570 nm, and comparison with standard curves. The polypeptides may be further characterized by sequence determination. This approach is especially useful for longer polypeptides, where amino acid composition data are inherently less informative. Sequence determination is carried out by sequential Edman degradation from the amino terminus, automated on a Model 470A gas-phase sequenator (Applied Biosystems, Inc.), by the methodology of R. M. Hewick et al., *J. Biol. Chem.*, 256, 7990 (1981).

The invention will be further described by reference to the following detailed examples.

EXAMPLE 1

Heparin Binding Assay

Figure 2:
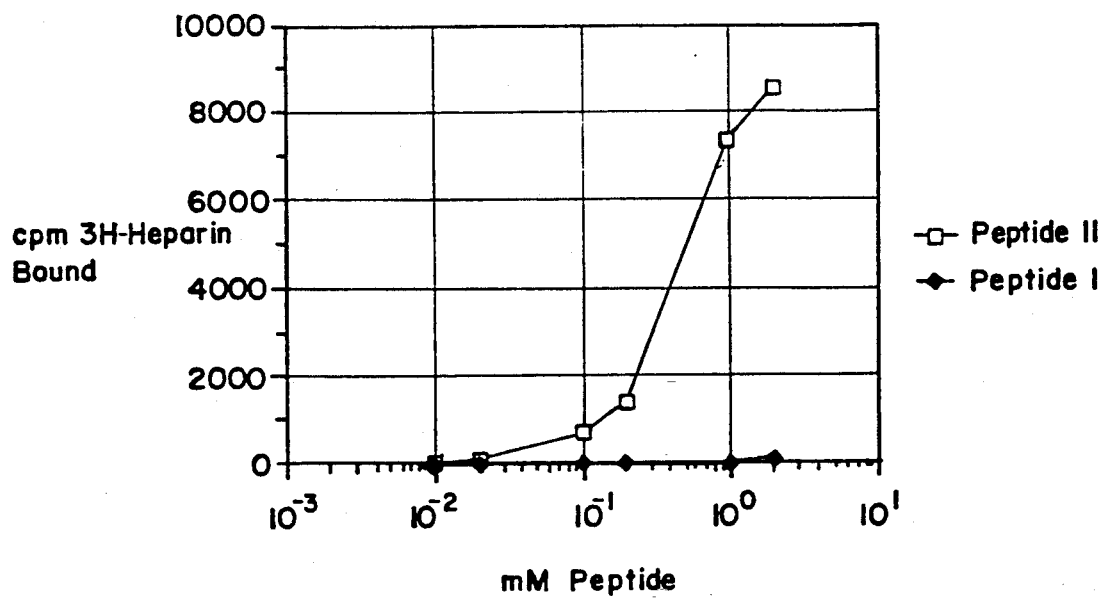
FIG. 2 is a graph depicting the heparin binding activity of peptides I and II of the invention.
Figure 3:
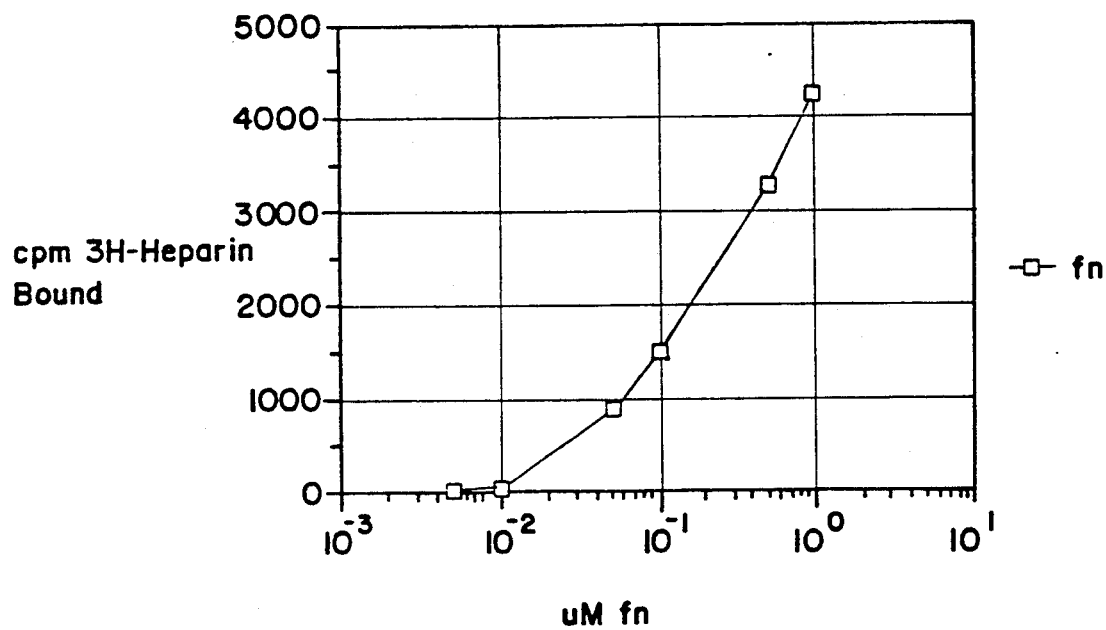
FIG. 3 is a graph depicting the heparin binding activity of fibronectin (fn).

The assay for heparin binding utilizes nitrocellulose sheets as substrata to bind peptides or proteins to be tested for heparin binding activity. Peptides I and II or intact fibronectin (fn) were solubilized in 50 mM $(NH_4)_2CO_3$ and diluted to the concentrations indicated in FIGS. 2 and 3. Nitrocellulose sheets which had been presoaked in 50 mM $NH_4CO_3$ were placed in a 96 well dot blot apparatus (Bethesda Research Laboratories, Bethesda, MD, and 250 µl of various concentrations of each peptide were aspirated through the wells. Each well was then washed three times with binding buffer (10 mM Tris-HCl, pH 8.0, 0.15M NaCl), and the filters were removed and allowed to air dry overnight. The filters were then equilibrated for 5 minutes at room temperature in binding buffer which contained 10 mM $CaCl_2$. $^3H$-heparin was then diluted to a concentration of 50,000 cpm/ml in binding buffer (with $Ca^{++}$), and nitrocellulose sheets were incubated in the presence of this mixture for 2 hours. The filters were then washed four times with binding buffer, and air dried. The individual spots of samples were cut out of the nitrocellulose and bound heparin was quantitated with a liquid scintillation counter. The results show that peptide II bound $^3H$-heparin in a concentration dependent manner (FIG. 2). In contrast, $^3H$-heparin bound poorly to peptide I at any concentration tested. The lowest concentration of peptide II which promoted $^3H$-heparin binding was $0.25 \times 10^{-3}M$ with a saturation of binding observed at higher coating concentrations $(0.25-0.5 \times 10^{-2}M)$. Similarly, fibronectin also bound $^3H$-heparin in a concentration dependent, saturable manner, with maximum binding observed at $10^{-6}M$ fibronectin (FIG. 3).

EXAMPLE 2

Neurite Outgrowth Assay

A. Preparation of Plates

Peptides I and II or intact fibronectin were diluted in Voller's buffer (0.05M Carbonate buffer, pH 9.6) and 100 µl of each concentration was dispensed into 96 well tissue culture plates in triplicate. The plates were then placed in a sterile hood overnight to evaporate the buffer and to dry the peptides onto the plate. The following morning, 200 µl of phosphate-buffered saline (PBS) containing 5 mg/ml bovine serum albumin (PBS/BSA) were added to each well and the plates were incubated for an additional 3 hours. At that point, the PBS/BSA was aspirated and cells in the appropriate media were added to each well.

B. Isolation of Neurons and Assay for Neurite Outgrowth

Embryonic CNS nerve cell cultures were prepared by the method of Rogers et al., *Devel. Biol.*, 98, 212-220 (1983). Briefly, spinal cords from 6-day chick embryos were isolated and their dorsal halves removed and placed in $Ca^{++}$-$Mg^{++}$ free (CMF) Hank's balanced salt solution for 10 minutes at 37° C. Only the ventral portions, containing predominantly motor neurons, were prepared for culture. The cords were then dissociated in 0.25% trypsin (Bactotrypsin, Difco) in CMF Hanks for 25 minutes at 37° C. The trypsin containing medium was replaced with Ham's F12, buffered with HEPES and supplemented with 10% fetal calf serum, and the cells repeatedly pipetted to complete dissociation. The single-cell suspension was pelleted by centrifugation, rinsed with Ham's F12-HEPES plus serum, centrifuged, and resuspended in Ham's F12 supplemented with sodium bicarbonate and glutamine (2 mM), penicillin (100 U/ml), streptomycin (100 U/ml) and plated into wells which had been prepared as described below in the presence and absence of the indicated concentrations of heparin. Cultures were incubated for 24 hours at 37° C. in a humidified incubator in 5% $CO_2$ and then fixed in glutaraldehyde. The number of neurons with neurites was quantitated by randomly sampling 10 fields with the aid of a dissecting microscope. The results of this assay are summarized on Tables I and II, below.

TABLE I

Comparison of Peptide I and Peptide II

| Coating Conc.* | Number of Neurons with Neurites | |
|---|---|---|
| | Without Heparin | With 10 μg/ml Heparin |
| I | 12;3 | 3 |
| II | 220;194 | 75 |
| Control (BSA) | 2 | 2 |

*500 μg/ml

TABLE II

Dose Response of Peptide II

| Coating Concentration of Peptide II | Number of Neurons with Neurites |
|---|---|
| 2 mg/ml | 39;70 |
| 1 mg/ml | 47;51 |
| 500 μg/ml | 47;32 |
| 250 μg/ml | 16;42 |
| Background | 8;8 |

These results indicate that peptide II is much more effective than peptide I at promoting neurite outgrowth, and that the neurite promoting activity of peptide II is apparently due to the heparin binding activity of this peptide. Thus, peptide II may be useful in providing a synthetic substratum to promote nerve growth in situations where nerve regeneration is desirable (e.g., in crush injuries).

EXAMPLE 3

Adhesion of Endothelial Cells

A. Isolation of Bovine Aortic Endothelial Cells

Bovine aortic endothelial cells were isolated according to the following protocol. Aortas were obtained from a local slaughterhouse, washed in cold phosphate buffered saline (PBS) (136 mM NaCl, 2.6 mM KCl, 15.2 mM $Na_2HPO_4$, pH 7.2) and processed within 2 hours. Crude collagenase (CLS III, 125-145 units per mg dry weight, Cooper Biomedical) was used at 2 mg/ml in Dulbecco's modified Eagle's medium (DMEM) (GIBCO). The vessel was clamped at the distal end, filled with the collagenase-PBS solution and digestion was carried out for 10 minutes. The lumenal contents were harvested, followed by the addition of fresh collagenase for two additional 10-minute periods. The enzyme-cell suspensions were added to an equal volume of DMEM containing 10% fetal bovine serum (FBS) to inhibit the enzyme and spun in a centrifuge at 400×g for 10 minutes. The resulting cell pellet was resuspended in DMEM containing 10% FBS, 100 units/ml of penicillin G, 100 μg/ml of streptomycin and 100 μg/ml of crude fibroblast growth factor. Cells are cultured in 75 $cm^2$ flasks in a humidified 5% $CO_2$ atmosphere at 37° C. Cultures were fed twice a week with the same medium and cells were used in assays when approximately 75% confluent. Cells were identified as endothelial in nature by characteristic cobblestone morphology, contact inhibition of growth upon reaching confluency, and positive immunofluorescent staining for factor VIII:RAg (Miles Laboratories) [S. Schwartz, In Vitro, 14, 966 (1978)]. Only endothelial cells, megakaryocytes and platelets are known to contain the factor VIII:RAg. This method routinely gives a high yield of endothelial cells with little contamination (less than 5%) by smooth muscle cells, pericytes or fibroblasts as judged by phase contrast microscopy as well as by immunostaining.

B. Aortic Endothelial Cell Adhesion Assay

Adhesion was measured using 96 well microtiter plates adsorbed with fibronectin or peptides I and II. Cultures of cells which were 60-80% confluent were metabolically labeled overnight with the addition of 10 μCi/ml of $^3H$.amino acids. On the day of the assay, the cells were harvested by trypsinization, the trypsin was inhibited by the addition of serum, and the cells were washed free of this mixture and resuspended in DMEM buffered with HEPES at pH 7.2. The adhesion medium also contained 5 mg/ml BSA. The cells were adjusted to a concentration of $3-4 \times 10^4$/ml, and 100 μl of this cell suspension was added to the wells. The assay mixture was then incubated at 37° C. for 90 minutes. At the end of the incubation, the wells were washed with warm PBS containing 10 mM $Ca^{++}$, and the adherent population was solubilized with 0.5N NaOH containing 1% sodium dodecyl sulfate. The solubilized cells were then quantitated using a liquid scintillation counter. Each determination was done in triplicate. The results of this study are summarized in Table III, below.

TABLE III

| Coating Concentration | Adherent Cells (Counts Per Minute) |
|---|---|
| Background | 403 |
| Peptide I | |
| 40 μg/ml | 1024 |
| 400 μg/ml | 1107 |
| 4000 μg/ml | 981 |
| Peptide II | |
| 40 μg/ml | 901 |
| 400 μg/ml | 1734 |
| 4000 μg/ml | 14,199 |
| Fibronectin | |
| 5 μg/ml | 13,714 |

These results indicate that peptide II is much more effective than peptide I at promoting endothelial cell adhesion, in agreement with the results observed for neurons. Thus, peptide II may be useful to promote endothelial cell adhesion to artificial or natural substrata.

EXAMPLE 4

Adhesion of Cancer Cells

A. Isolation of Metastatic Melanoma Cells

Highly metastatic melanoma cells, K1735M4, were originally provided by Dr. I. J. Fidler of Houston, TX. When the cells were received, a large number of early passage cells were propagated and frozen in liquid nitrogen. The tumor cells are usually cultured in vitro for no longer than six weeks. Following this period, the cells are discarded and new cells withdrawn from storage for use in further in vitro or in vivo experiments. This precaution is taken to minimize phenotypic drift that can occur as a result of continuous in vitro passage. The cells were cultured in Dulbecco's Modified Eagle's Medium containing 5% heat inactivated fetal calf serum. The cultures were grown in 37° C. incubators with a humidified atmosphere containing 5% $CO_2$. Cells were subcultured twice weekly by releasing cells gently from the flask, using 0.05% trypsin and 1 mM EDTA.

The melanoma cells were pulsed in the same fashion as the endothelial cells described hereinabove, except that 2 μCi/ml $^3$HTd(tritiated thymidine) was added to each culture instead of amino acids. The labeled cells were harvested as described for the endothelial cells. The cell adhesion assay was identical to that described hereinabove for the bovine aortic endothelial cell assay. The results of this assay are summarized on Table IV, below.

TABLE IV

Tumor Cell Adhesion*

| Coating Concentration | Adherent Cells (Counts Per Minute) |
| --- | --- |
| Background | 1400 |
| Peptide I | |
| 40 μg/ml | 3900 |
| 200 μg/ml | 3500 |
| 400 μg/ml | 3000 |
| 2000 μg/ml | 4000 |
| Peptide II | |
| 400 μg/ml | 4600 |
| 200 μg/ml | 4700 |
| 400 μg/ml | 4300 |
| 2000 μg/ml | 3900 |
| Fibronectin | |
| 1 μg/ml | 4700 |
| 10 μg/ml | 7900 |
| 50 μg/ml | 11,000 |
| 100 μg/ml | 9700 |

*Measured one hour following the start of the assay.

In contrast to the results obtained above using neurons and endothelial cells, peptides I and II are both capable of promoting the adhesion of melanoma cells. This may suggest cell specific differences in the adhesion of cells to this region of fibronectin.

A number of practical applications for polypeptides I and II can be envisioned. Such applications include the promotion of the healing of wounds caused by the placement of natural synthetic substrata within the body. Such synthetic substrata can include artificial vessels, intraocular contact lenses, hip replacement implants and the like, where cell adhesion is an important factor in the acceptance of the synthetic implant by normal host tissue.

As described in U.S. Pat. No. 4,578,079, medical devices can be designed making use of these polypeptides to attract cells to the surface in vivo or even to promote the growing of a desired cell type on a particular surface prior to grafting. An example of such an approach is the induction of endothelial cell growth on a prosthetic device such as a blood vessel or vascular graft, which is generally woven or knitted from a synthetic resin such as nitrocellulose, expanded polytetrafluoroethylene or polyester fiber, particularly Dacron TM (polyethylene terephthalate) fiber. Devices intended for cardiac insertion include temporary left ventricular assist devices, heart valves, intraortic ballon pumps and artificial hearts. Such devices are preferably formed from synthetic resins such as polyether-type polyurethane elastomers (Cardiothane TM, Kontron) or from vulcanized polyolefin rubbers (Hexsyn TM, Goodyear).

Most types of cells are attracted to fibronectin and to the present polypeptides, but endothelial cells, epithelial cells and fibroblastic cells in particular are attracted to the present polypeptides. The latter point indicates the potential usefulness of these defined polypeptides in coating a patch graft or the like for aiding wound closure and healing following an accident or surgery. The coating and implantation of synthetic polymers may also assist in the regeneration of nerves following crush traumae, e.g., spinal cord injuries.

In such cases, it may be advantageous to couple the peptide to a biological molecule, such as collagen, a glycosaminoglycan or a proteoglycan. Collagens, proteoglycans and glycosaminoglycans are major components of connective tissues and basement membranes. In some cases, prosthetic devices formed entirely or in part from naturally-occurring tissues instead of synthetic polymers are used. One example is the use of porcine heart valves to replace defective human heart valves. Such artificial valves can also comprise human dura matter or bovine pericardium. Another example is the use of bovine arteries as vascular grafts.

It may be useful to coat surfaces of these biological substrata with the present polypeptides, in order to modify the cellular response, in vivo, thus improving the therapeutic outcome. This can be achieved by a variety of methods known to the art, e.g., by direct binding of the polypeptides to the target surfaces based on the affinities described hereinabove, or by the covalently bonding the polypeptides to the substrate using various crosslinking reactions or reagents. For a review of the use of synthetic resins and biomaterials in prosthetic devices, see Chem. & Eng. News (Apr. 14, 1986) at pages 30–48, the disclosure of which is incorporated by reference herein.

It is also indicative of their value in coating surfaces of a prosthetic device which is intended to serve as a temporary or semipermanent entry into the body, e.g., into a blood vessel or into the peritoneal cavity, sometimes referred to as a percutaneous device. Such devices include controlled drug delivery reservoirs or infusion pumps.

Also, polypeptides I and II can be used to promote endothelial, fibroblast or epithelial cell adhesion to naturally occurring or artificial substrata intended for use in vitro. For example, a culture substrate such as the wells of a microtiter plate or the medium contacting surface of microporous fibers or beads, can be coated with the cell-attachment polypeptides. This can obviate the use of fibronectin in the medium, thus providing better defined conditions for the culture as well as better reproducibility.

As one example of commercial use of cell-attachment surfaces, Cytodex particles, manufactured by Pharmacia, are coated with gelatin, making it possible to grow the same number of adherent cells in a much smaller volume of medium than would be possible in dishes. The activity of these beads is generally dependent upon the use of fibronectin in the growth medium and the present polypeptides are expected to provide an improved, chemically-defined coating for such purposes. Other surfaces or materials may be coated to enhance attachment, such as glass, agarose, synthetic resins or long-chain polysaccharides.

The invention has been described with reference to various specific and preferred embodiments and techniques. However, it should be understood that many variations and modifications may be made while remaining within the spirit and scope of the invention.

What is claimed is:

1. A prosthetic device designed for placement in vivo, comprising a surface coated with a composition consisting essentially of a polypeptide of the formula:

tyr—glu—lys—pro—gly—ser—pro—pro—arg—glu—val—val—pro—arg—pro—arg—pro—gly—val.

lys—asn—asn—gln—lys—ser—glu—pro—leu—ileu—gly—arg—lys—lys—thr—asp—glu—leu, or mixtures thereof.

2. The prosthetic device of claim 1, wherein said surface constitutes a portion of a vascular graft.

3. The prosthetic device of claim 1, wherein said surface constitutes a portion of an intraocular contact lens.

4. The prosthetic device of claim 1, wherein said surface constitutes a portion of a heart valve.

5. The prosthetic device of claim 1, wherein said surface constitutes a portion of a hip replacement implant.

6. The prosthetic device of claim 1, wherein said surface constitutes a portion of a percutaneous device.

7. A prosthetic device of claim 1 wherein said surface is made of a synthetic resin.

8. A prosthetic device in accordance with claim 7 wherein said synthetic resin is selected from the group consisting of nitrocellulose, polyurethane, expanded polytetrafluoroethylene, polyester and polyolefin.

9. A prosthetic device of claim 1 wherein said surface is made of a naturally-occurring tissue.

* * * * *